March 5, 1968 G. DE RUITER Plant Pat. 2,799
ROSE PLANT
Filed July 21, 1966
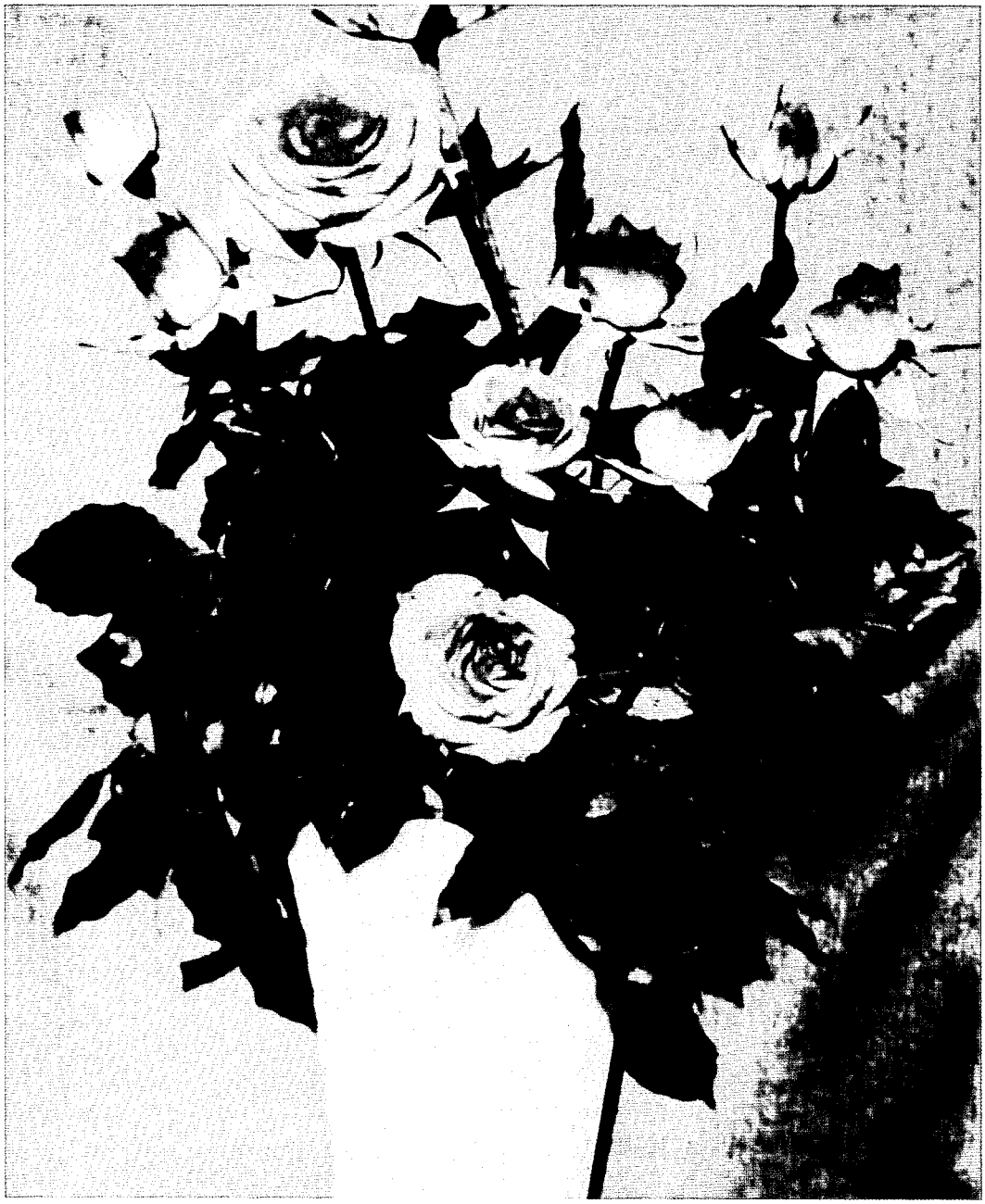
Inventor.
Gijsbert de Ruiter
By: Robb & Robb
Attorneys.

United States Patent Office

Plant Pat. 2,799
Patented Mar. 5, 1968

2,799
ROSE PLANT

Gijsbert de Ruiter, Hazerwoude, Netherlands, assignor to Carlton Rose Nurseries, Inc., Carlton, Oreg., a corporation of Oregon Filed July 21, 1966, Ser. No. 567,036
1 Claim. (Cl. Plt.—22)

The present invention relates to a new and distinct variety of rose plant of the floribunda class, which was originated by me by crossing the variety known as "Orange Sensation" (unpatented) with the variety known as "Circus" (U.S. Plant Patent No. 1382).

As the result of this breeding, I have produced a new and improved rose variety which is distinguished from its parents, as well as from all other rose varieties, as evidenced by the following unique combination of characteristics which are outstanding therein:

(1) Attractive shiny and glossy foliage;

(2) Strong and upright flower stems, with little or no "blind" wood;

(3) A distinctive and attractive general color tonality of the flowers corresponding to burnt orange and gold in the opening stage, changing to pink as the flowers fully open and mature;

(4) Very long keeping qualities of the flowers both on the bush and as cut flowers; and (5) Good shipping qualities.

A sexual reproduction of my new variety by both budding and grafting as performed at Hazerswoude, Holland and at Hillsboro, Oreg., U.S.A., shows that the foregoing characteristics and distinctions come true to form and are established and transmitted through succeeding propagations:

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Wilson Color Chart as prepared in collaboration with the Royal Horticultural Society, except where general color terms of ordinary dictionary significance are obvious:

Type: Hardy; bush; greenhouse and outdoor; seedling; for cut flowers and for garden decoration.

Class: Floribunda.

Breeding: Seedling.

*Seed parent.*—"Orange Sensation."

*Pollen parent.*—"Circus."

Propagation: Holds its distinguishing characteristics through succeeding propagations by both budding and grafting.

*Flower*

Locality where grown and observed: Hillsboro, Oreg., U.S.A.

Continuity: Continuous.

Flowers Borne: Singly and from two to several to stem; in irregular clusters; on strong, long stems.

Quantity of bloom: Free, both outdoors and in greenhouse.

Fragrance: Slight. Nature—tea.

Bud:

*Peduncle.*—Long; medium caliper; stiff; medium smoothness; with numerous yellow hairs. Color—medium green.

*Before calyx breaks.*—Size—medium. Form—pointed oval; without foliaceous appendages on the surface of the bud; without foliaceous parts extending beyond the tip of the bud. Color—Marigold Orange, Plate 11/2.

*As calyx breaks.*—*Color*—Marigold Orange, Plate 11/1 over center, shading to Scarlet, Plate 19/1 about upper edge, with Lemon Yellow, Plate 4/2 at base.

*As first petal opens.*—Size—small. Form—short; pointed. Color: outside—Marigold Orange, Plate 11/1 over center, shading to Scarlet, Plate 19/1 about upper edge, with Lemon Yellow, Plate 4/2 at base; inside—Marigold Orange, Plate 11/0 over center, shading to Scarlet, Plate 19/0 about upper edge, with Lemon Yellow, Plate 4/2 at base.

*Opening.*—Opens up well.

Bloom:

*Size (when fully open).*—From 2 inches to 2½ inches.

*Petalage.*—Double; from 20 to 30 petals; arranged regularly.

*Form.*—Cupped at first, but becoming open; petals being at first cupped outward, but later becoming loosely cupped outward at maturity.

Petals:

*Texture.*—Thick; leathery.

*Appearance.*—Inside—satiny. Outside—shiny.

*Shape.*—Outside—round, with apex flat and with 1 notch. Intermediate—round, with 1 notch. Inside—round, with 1 notch.

This description of a newly opened flower was made from a rose grown in a greenhouse during the month of September at Hillsboro, Oreg., U.S.A.:

*Color.*—Outer petals—Marigold Orange, Plate 11/1 over center, shading to Scarlet, Plate 19/1 about upper edge, with Lemon Yellow, Plate 4/2 at base. Inner petals—Marigold Orange, Plate 11/0 over center, shading to Scarlet, Plate 19/0 about upper edge, with Lemon Yellow, Plate 4/0 at base.

This description was made from a rose that was open for five days indoors during the month of September at Hillsboro, Oreg., U.S.A.:

*Color.*—Outer petals—Saffron Yellow, Plate 7/1 over center, shading to Camellia Rose, Plate 622 about upper edge, with Aureolin, Plate 3/1 at base. Inner petals—Saffron Yellow, Plate 7/0 over center, shading to Camellia Rose, Plate 622 about upper edge, with Aureolin, Plate 3/1 at base.

*General color effect.*—Newly opened flower—vermillion from edge to yellow at base. 5-days open—pink from edge to pale yellow at base. Commercially—a riot of burnt orange and gold, at first, and then fading to pink when fully open and mature.

*Behavior.*—Drop off cleanly; fading brown.

*Flower longevity.*—On bush in garden—8 days in September. Cut roses grown outdoors and kept at living-room temperatures—8 days in September. Cut roses grown in greenhouse and kept at living-room temperatures—8 days in September.

*Reproductive organs*

Stamens: Many; arranged regularly about pistils. Color—Lemon Yellow, Plate 4/1.

Filaments: Medium length; many; most with anthers. Color—yellow.

Anthers: Medium size; all open at once. Color—yellow.

Pollen: Moderate quantity. Color—yellow.

Pistils: Medium number.

Styles: Uneven; medium length; thin; bunched.

Stigma: Color—yellow.

Ovaries: All enclosed in calyx.

Hips: Globular; with a conspicuous neck; smooth; walls thin. Color—reddish.

Sepals: Permanent; long; spear-shaped; recurved. Color—Lettuce Green, Plate 861/1.

Seeds: Many; medium size.

*Plant*

Foliage:

*Leaves.*—Compound of 5–7 leaflets; normal abundance; medium large size; moderately leathery.

*Leaflets.*—Shape—oval. Apex—acute. Base—round. Margin—simply serrate.

*Color.*—Mature: upper surface—dark green; under surface—normal green. Young: upper surface—bronze; under surface—greenish bronze.

*Rachis (the supporting stem of the compound leaf)*—Medium caliper. Upper side—hairy. Under side—sparsely prickly.

*Stipules.*—Medium length; with short points turning out at an angle of more than 45°.

*Disease resistance.*—Very good resistance to mildew and blackspot (better than either of parent varieties), as determined from comparison with other varieties grown under the same cultural conditions at Hillsboro, Oreg., U.S.A.

Growth:

*Habit.*—Bushy.

*Growth.*—Vigorous.

*Canes.*—Medium heavy.

*Main stems.*—Color—green. Thorns—several; medium long; hooked downward; with long, narrow base. Prickles—none. Hairs—none.

*Branches.*—Color—green. Thorns—several; medium long; hooked downward; with long, narrow base. Prickles—none. Hairs—none.

*New shoots.*—Color—bronze-red. Thorns—several; medium long; hooked downward; with long, narrow base. Prickles—none. Hairs—none.

I claim:

1. A new and distinct variety of rose plant of the floribunda class, substantially as herein shown and described, characterized particularly as to novelty by the unique combination of attractive shiny and glossy foliage, strong and upright flower stems, with little or no "Blind" wood, a distinctive and attractive general color tonality of the flowers corresponding to burnt orange and gold in the opening stage, changing to pink as the flowers fully open and mature, very long keeping qualities of the flowers both on the bush and as cut flowers; and good shipping qualities.

No references cited.

ROBERT E. BAGWILL, *Primary Examiner.*